United States Patent [19]

Blaszkiewicz et al.

[11] Patent Number: 5,004,835

[45] Date of Patent: Apr. 2, 1991

[54] SUBSTITUTED DICARBOXYLIC ACID-BIS(3,5-DICARBAMOYL-2,4,6-TRIIODOANILIDES), PROCESS FOR THEIR PRODUCTION AS WELL AS X-RAY CONTRAST MEDIA CONTAINING THEM

[75] Inventors: Peter Blaszkiewicz; Ulrich Speck, both of Berlin, Fed. Rep. of Germany

[73] Assignee: Schering Aktiengesellschaft, Berlin and Bergkamen, Fed. Rep. of Germany

[21] Appl. No.: 271,464

[22] Filed: Nov. 15, 1988

[30] Foreign Application Priority Data

Nov. 16, 1987 [DE] Fed. Rep. of Germany ....... 3739098

[51] Int. Cl.$^5$ .................... C07C 63/24; C07C 103/78
[52] U.S. Cl. ........................ 564/153; 424/5
[58] Field of Search ................. 424/5; 564/153

[56] References Cited

U.S. PATENT DOCUMENTS 4,239,747 12/1980 Pfeiffer et al. ......................... 424/5
4,426,371 6/1984 Pfeiffer et al. ......................... 424/5

Primary Examiner—Richard L. Raymond
Assistant Examiner—Brian Bembenick
Attorney, Agent, or Firm—Millen, White & Zelano

[57] ABSTRACT

The invention relates to new substituted dicarboxylic acid-bis(3,5-dicarbamoyl-2,4,6-triiodoanilines), of general formula I

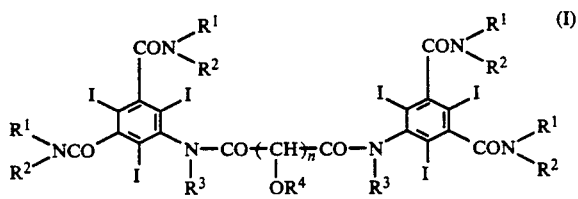

in which $R^1$ means a hydrogen atom, a $C_1$–$C_4$ alkyl radical or $R^2$, wherein $R^1$ and $R^2$ are the same or different, $R^2$ means a straight-chain or branched-chain $C_2$ – $C_8$ monohydroxyalkyl radical or polyhydroxyalkyl radical, $R^3$ means a hydrogen atom, a $C_1$–$C_4$ alkyl radical or $R^2$, $R^4$ means a hydrogen atom or a $C_1$–$C_4$ alkyl radical, and n=1 or 2.

The new nonionic compounds of formula I because of their good pharmacological and physiocochemical properties are outstandingly suitable as radiopaque substances in X-ray contrast media for use in all the fields of applications of X-ray contrast media.

17 Claims, No Drawings

SUBSTITUTED DICARBOXYLIC ACID-BIS(3,5-DICARBAMOYL-2,4,6-TRIIODOANILIDES), PROCESS FOR THEIR PRODUCTION AS WELL AS X-RAY CONTRAST MEDIA CONTAINING THEM

BACKGROUND OF THE INVENTION

X-ray contrast media are indispensable auxiliary agents in the diagnosis of numerous diseases, such as, for example, arteriosclerotic vascular processes, tumors, infarcts, diseases of the kidneys and efferent urinary passages. Since the introduction of the first products, great advances have been made.

The chemotoxic properties of the X-ray contrast media have been greatly reduced. For clinical use this means less occurrence of side effects such as nausea, vomiting, certain circulatory reactions, urticaria, bronchial spasm and other symptoms up to shock and death. Chemotoxic effects, e.g., as $LD_{50}$, are pharmacologically measurable after intravenous injection.

The products used were very strongly hypertonic (e.g., up to 8 times the osmolality of blood) and consequently caused a great number of potentially serious side effects, such as, e.g., drop in blood pressure, bradycardia to cardiac arrest, disturbances of the blood-brain barrier, intense pain, etc. Newer contrast media, used in clinically customary concentrations, exhibit only 2 to 3 times the osmolality of the blood.

Although both the chemotoxicity and the hypertonicity of the contrast media were lowered, so far no ideal values could be achieved.

Even the latest so-called nonionic contrast media still caused serious and very serious incidents (McClennan, Radiology 162, 1:1-8 [1987]: "Low-osmolality contrast media: Premises and Promises"), which have to be ascribed to chemical-toxic actions.

Also the osmolality of these products is still much too high to be able to speak of physiological contrast media. Therefore it is not surprising that at least a certain percent of patients complain about the intense pain during the examination with these products. ("Pain and hemodynamic effects in aortofemora angiography" in Acta Radiol. Diagnosis 23, 4:289-399 [1982]).

From experience these problems can be solved to a large extent by synthesis of water-soluble, very hydrophilic "nonionic dimers," i.e., of contrast media molecules, which consist of the linkage of 2 triiodinated aromatic substances. Such substances were first described in DOS 26 28 517. Since then a series of very similar structures has been described, e.g., in DOS 28 05 928, EP 0023992, EP 0049745 and EP 0108638.

Nonionic dimers are generally not hypertonic in comparison with the body fluids in all the concentrations customary for X-ray diagnosis. Further, some representatives of this substance class exhibit a very slight chemotoxicity, i.e., extremely high $LD_{50}$ values are achieved after intravenous injection.

Despite these advantages, contrast media with a base of nonionic dimers thus far have hardly had any clinical use. The reason for this is the viscosity, especially of highly concentrated solutions, which are necessary for certain especially critical angiographic examinations. Thus, angiographic examinations of the coronary vessels and ventricles are to be selectively performed only with contrast media solutions which contain 350 mg of more of iodine/ml.

In this case the contrast media solutions must be injected with very high speed through about 100-cm long very narrow catheters. Solutions with over 12 to 15 cp at 37° C. are hardly any longer suitable for the purpose. But also for very fast intravenous injection, as is necessary for various modern x-ray techniques, very well tolerated and slightly viscous contrast media are necessary.

The viscosity of the nonionic dimer contrast media depends on a series of factors, of which the iodine content of the molecules plays an essential role. With an increasing iodine content the viscosity of the solutions of the respective molecules decreases, but at the same time so does their solubility in water.

It is desirable to make available in high concentrations very well tolerated and water-soluble blood isotonic and at the same time slightly viscous contrast media with high iodine content.

SUMMARY OF THE INVENTION

The invention relates to new substituted dicarboxylic acid-bis(3,5-dicarbamoyl-2,4,6-triiodoanilides), of general formula I

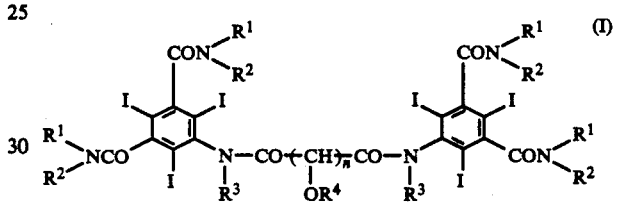

in which $R^1$ means a hydrogen atom, a $C_1$-$C_4$ alkyl radical or $R^2$, wherein $R^1$ and $R^2$ may be the same or different, $R^2$ means a straight-chain or branched-chain $C_2$-$C_8$ monohydroxyalkyl radical or polyhydroxyalkyl radical, $R^3$ means a hydrogen atom, a $C_1$-$C_4$ alkyl radical or $R^2$, wherein $R^2$ and $R^3$ may be the same or different, $R^4$ means a hydrogen atom or a $C_1$-$C_4$ alkyl radical, and n=1 or 2, process for their production of these compounds as well as X-ray contrast media containing compounds of formula I as the radiopaque substance and a method of performing X-ray imaging using the X-ray contrast media, e.g., rendering independently radiopaque a hollow or fluid filled body part.

Radicals $R^1$, $R^3$ and $R^4$ independently can be lower alkyl radicals, preferably straight chain radicals with 1 to 4 carbon atoms, preferably methyl, ethyl, propyl and butyl radicals. The methyl radicals are particularly suitable.

The radical $R^2$ is a straight-chain or branched-chain monohydroxyalkyl radicals or straight or branched chain polyhydroxyalkyl radicals with 2 to 8 carbon atoms, preferably 2 to 5 carbon atoms. Straight-chain radicals of $R^2$ have most preferably 2 to 4 carbon atoms, and branched-chain radicals have most preferably 3 to 5 carbon atoms. The hydroxy groups in the radical $R^2$ can be present as primary or secondary hydroxy groups. The radical $R^2$ can contain 1 to 5 hydroxy groups: preferably 1 to 3 hydroxy groups. As radical $R^2$ there can be mentioned, for example: the 2-hydroxyethyl, 2-hydroxypropyl, 3-hydroxypropyl, 2,3-dihydroxypropyl, 1-hydroxymethyl-2-hydroxyethyl, 2,3-dihydroxybutyl, 2,4-dihydroxybutyl, 3,4-dihydroxybutyl, 3-hydroxy-2-(hydroxymethyl)propyl, 2,3-dihydroxy-1-methylpropyl, 2-hydroxy-3-(hydroxymethyl)-butyl, 2,3,4-trihydroxybutyl, 2,4-dihydroxy-3-(hydroxymethyl)-butyl, 3-hydroxy-2,2-bis-(hydroxymethyl)-propyl, 4-hydroxy-3,3-bis-(hydroxymethyl)-butyl, 4-hydroxy,2,2-bis-(hydroxymethyl)-butyl, 2-hydroxy-1,1-bis-(hydroxymethyl)-ethyl, 1,3-dihydroxy-isopropyl, 2,3-dihydroxy-1-hydroxy methylpropyl radical, etc.

DETAILED DISCUSSION

It was found, surprisingly, that an aqueous solution of the compounds of formula I according to the invention, have excellent compatibility and blood isotonia. In addition, they have, even at concentrations of 300 to 400 mg of iodine/ml, the desired sufficiently low viscosity to make possible a universal application in angiography both for the fast addition mode and in the application of highly concentrated solutions through narrow catheters.

The compounds according to the invention of general formula I thus are outstandingly suitable as radiopaque substances for production or for use in all applications for X-ray contrast media. The new compounds have all the properties which are required of X-ray contrast media. Many, although nonionic, are very easily water-soluble. The new compounds represent outstandingly compatible X-ray contrast media, which are suitable in angiography, urography, myelography, lymphography and for representing various body cavities and for other radiological examinations.

Because of their faint and neutral taste some of the compounds are outstandingly suitable for oral application and for introduction into the lung. The bitter and nauseating taste inherent in the usual contrast media is to be considered as a serious drawback especially in gastrography and bronchography.

The invention thus also relates to new x-ray contrast media based on the compounds of the general formula I. Production of the new X-ray contrast media based on the compounds of general formula I according to the invention takes place in a way known in the art, e.g., in that the radiopaque substance is put in a form suitable for intravenous application with the additives usual in galenicals, e.g., stabilizers such as sodium edetate, calcium disodium edetate, physiologically compatible buffers, sodium chloride,. etc. The concentration of the new X-ray contrast media in the aqueous medium fully conforms with the conventional X-ray diagnostic method. The preferred concentrations and dosages of the new compounds are in the ranges of 50–500 mg I/ml for the concentration and 5–500 ml for the dosage. Concentrations between 100 and 40 mg I/ml are especially preferred.

The invention further relates to a process for the production of the compounds of general formula I, which is characterized in that in a way known in the art.

A substituted dicarboxylic acid derivative of general formula II

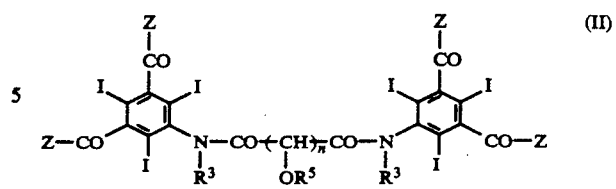

in which $R^3$ means a hydrogen atom or a $C_1$–$C_4$ alkyl group,
$R^5$ means a $C_1$–$C_4$ alkyl group, benzyl group or a $C_1$–$C_6$ acyl group,
Z means a reactive acid radical or ester radical and
n = 1 or 2, is reacted with a base of general formula III

in which $R^{1'}$ means a hydrogen atom or a $C_1$–$C_4$ alkyl radical or $R^{2'}$ and $R^{1'}$ and $R^{2'}$ are the same or different,
$R^{2'}$ means a straight-chain or branched-chain $C_2$–$C_8$ monohydroxy alkyl radical or polyhydroxy alkyl radical in free or protected form, optionally the aromatic acylamino groups are reacted to $C_1$–$C_4$ N-alkyl or N-hydroxy alkyl acylamino compounds and/or optionally the protected hydroxyl groups are released.

If $R^5$ is an acyl group in general formula II, monocarboxylic acids are used with 1–6 carbon atoms. The acyl groups of acetic, propionic, butyric and benzoic acid are suitable. The acyl group of benzoic acid is particularly suitable.

As reactive acid radicals and ester radicals for Z the acid halides, especially acid chlorides and bromides, but also others, such as, for example, the examples published in Tetrahedron 36, 3409 (1980), are used.

For the amidizing reaction of the compound of formula II with the base of formula III the hydroxyl groups contained in groups $R^{1'}$ and $R^{2'}$ can be present in free or protected form. If these hydroxyl groups are to be present in protected form, all hydroxyl protecting groups are suitable, which are, as is known, suitable for an intermediate hydroxyl group protection, i.e., which can easily be introduced and, with re-formation of the ultimately desired free hydroxyl group, can also be easily cleaved off again. Protection by esterification is preferred, e.g., by introduction of the benzoyl or acyl, especially of the acetyl radical. Suitable protecting groups are also ether groups such as, for example, benzyl, di- and tri-phenyl methyl ether groups as well as acetal and ketal groups with, e.g., acetaldehyde and acetone.

Also cyclic ketals, such as, for example, dioxane and dioxepin derivatives are used. The 6-amino-2,2-dimethyl-1,3-dioxepin-5-ol [European patent application, publication number 0033426] is especially suitable.

Amidation of the two carboxyl groups, which are present as reactive acid radical or ester radical Z, takes place in a suitable solvent at 0° C. to 120° C., preferably at 20° C. to 100° C. Suitable solvents are, inter alia, polar solvents such as, for example, water, dioxane, tetrahydrofuran, dimethylformamide, dimethylacetamide, hexametapol, acetone and the like and their mixtures. Since in the amidation reaction per reacted molecule of the compound of formula II two moles of acid (from the reactive acid radical or ester radical) are freed, which must be neutralized, for each reactive acid group or ester group two equivalents of base are required, suitably in excess of at least 10%. For practical implementation, the dissolved or suspended starting compound of formula II is mixed with at least 4.4 equivalents of the base of formula III or with at least 2.2 equivalents of the base of formula III and additionally with at least 2.2 equivalents of a base different from III, which then acts as a proton acceptor. Tertiary amines are advantageously used as proton acceptors, such as, for example, triethylamine, tributylamine, pyridine or dimethylaminopyridine or inorganic bases such as, for example sodium bicarbonate, sodium carbonate or the corresponding potassium salts and their hydrates. The inorganic and organic salts resulting in the course of the reaction are separated in a known way, e.g., by use of ion exchanger acids or bases or by filtration over known adsorbents such as, for example, diaion or Amberlite ® XAD-2 and 4.

The optionally subsequent N-alkylation of the aromatic acylamino groups also takes place according to methods known to one skilled in the art, e.g., in polar solvents such as alkanols or alkanediols such as methanol, ethanol or propanediol or in polyethers such as ethylene glycol diethyl ether, diethylene glycol dimethyl ether, inter alia, or their mixtures in the presence of strong bases, such as alcoholates of sodium potassium or their hydrides.

In case $R^3$ means a lower alkyl or hydroxy alkyl, the alkyl halides or hydroxy alkyl halides or sulfates or their equivalents are used as alkylation agents. They are, for example, methyl iodide, methyl bromide or dimethyl sulfate for compounds of formula I with $R^3$=methyl or ethyl bromide, ethyl iodide or diethyl sulfate for compounds of formula I with $R^3$=ethyl or chloroethanol or bromoethanol for compounds of formula I with $R^3$=hydroxyethyl or chloropropanediol or bromopropanediol for compounds of formula I with $R^3$=dihydroxypropyl.

Cleavage of the protecting groups present takes place under the respectively necessary conditions. Ketals, for example, are cleaved off by mineral acids in one-phase organic aqueous solutions at temperatures between 0° C. and the boiling temperature of the reaction mixture. A ketal can be cleaved off especially easily in a tetrahydrofuran-water mixture (1:1) by addition of half-concentrated hydrochloric acid. The temperature range between 10° and 40° C. is particularly suitable. methods known in the literature, for example, with sodium in alcohols or liquid ammonia (Advances in Carbohydrat, Chem. 12, 149 [1957], J. Org. Chem. 29, 3725 [1964].

Saponification of the acyloxy groups can take place in a way known in the art. For example, with bases in an aqueous alcoholic solution, as with sodium hydroxide in aqueous methanolic solution.

The initial products of general formula II used according to the process can be produced according to processes known in the art, for example, from 5-amino-2,4,6-triiodoisophthalic acid dichloride (German laid-open specification 2031724).

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application(s) West German P. 37 39 098.8, filed Nov. 16, 1987, (the priority document), are hereby incorporated by reference.

EXAMPLES

Production of initial compounds Acetoxymalonic acid bis[3,5-bis(chlorocarbonyl)-2,4,6-triodoanilide]

119.14 g (200 mmol) of 5-amino-2,4,6-triiodoisophthlatic acid dichloride (German laid-open specification 2031724) is dissolved in 1.2 liters of toluene at 100° C. and 21.9 g (110 mmol) of acetoxymalonic acid chloride dissolved in 50 ml of toluene is instilled into this solution. A crystalline precipitate is immediately formed. When the addition is finished, the heating bath is removed, cooling to room temperature is performed and the crystallizate is suctioned off. 100.5 g=76.3 mmol=76.3% of theory of acetoxymalonic acid bis[3,5-bis(chlorocarbonyl)-2,4,6-triiodoanilide] is obtained. Acetoxymalonic acid bis[3,5-bis(chlorocarbonyl)-2,4,6-triiodo-N-methylanilide]

182.9 g (300 mmol) of 5-methylamino-2,4,6-triidoisophthalic acid dichloride is dissolved in 900 ml of toluene, the solution is heated to 85° C. and at this temperature 32.83 g (165 mmol) of acetoxymalonylchloride, dissolved in 65 ml of toluene, is instilled. The product crystallizes immediately from the hot solution. It is cooled to room temperature, the precipitate is suctioned off and dried in a vacuum at 50° C. The yield is 166.7 g=123.9 mmol=82.6% of theory of acetoxymalonic acid bis[3,5-bis(chlorocarbonyl)-2,4,6-triiodo-N-methylanilide ].

Methoxymalonic acid bis[3,5-bis(chlorocarbonyl)-2,4,6-triiodo-N-methylanilide 182.92 g (300 mmol) of 5-methylamino-2,4,6-triiodoisophthalic acid dichloride is dissolved in 900 ml of toluene, the solution is heated to 85° C. and 28.2 g (165 mmol) of methoxymalonylchloride is instilled within 30 minutes. The reaction product immediately crystallizes out. After about 2 hours, it is cooled to room temperature, the product is suctioned off, washed with toluene and dried in a vacuum at 50° C. The yield is 155.14 g=117.75 mmol=78.5% of theory of methoxymalonic acid bis[3,5-(chlorocarbonyl)-2,4,6-triiodo-N-methylanilide].

Methoxymalonic acid bis[3,5-bis(chlorocarbonyl)-2,4,6-triiodoanilide]]

119.14 g (220 mmol) of 5-amino-2,4,6-triodoisophthalic acid dichloride is dissolved in 1.2 liters of toluene at 100° C. and 18.8 g (110 mol) of methoxyacetylchloride is instilled into this solution within 30 minutes. The reaction product precipitates from the reaction solution as crystals. 1 hour after addition of the acid chloride, it is cooled to room temperature, the crystallizate is suctioned off, washed with toluene and dried in a vacuum at 50° C. The yield is 102.64 g=78.6 mmol=79.6% of theory of methoxymalonic acid bis[3,5-bis(chlorocarbonyl)-2,4,6-triiodoanilide].

2,3-diacetoxysuccinic acid bis[3,5-bis(chlorocarbonyl)-2,4,6-triiodo-N-methylanilide]

61 g (100 mmol) of 5-methylamino-2,4,6-triiodoisophthalic acid dichloride is dissolved in 600 ml of toluene, the solution is heated at 80° C. and 13.55 g (50 mmol) of 2,3-diacetoxysuccinic acid dichloride (D. Seebach et al. Ber. 1980, 1691), dissolved in 30 ml of toluene, is instilled. The product already crystallizes out at higher temperature. After 1 hour, it is cooled to room temperature, the crystallizate is suctioned off, washed toluene and dried in a vacuum. The yield is 51.5 g=36.15 mmol=72.3% of theory of 2,3-diacetoxysuccinic bis[3,5-bis(chlorocarbonyl)-2,4,6-triiodo-N-methylanilide]

Benzyloxymalonic acid bis[3,5-bis(chlorocarbonyl)-2,4,6-triiodoanilide 70.4 g (130 mmol) of a 5-amino-2,4,6-triiodoisophthalic acid dichloride is dissolved in 700 mol of toluene at 100° C. and 16.06 g (65 mmol) of benzyloxymalonic acid dichloride (produced similarly to Hammond et al. Soc. 1957, 1062) is added to this solution. After a few minutes the bisanilide precipitates out as crystalline precipitate. After 30 minutes the heating is removed, cooling to room temperature is performed, the precipitate is suctioned off, washed with toluene and dried in a vacuum at 50° C. 60.18 g (44.07 mmol)=67.8% of theory of crystallizate is obtained. Melting point: is greater than 350° C.

Benzyloxymalonic acid bis[3,5-bis(chlorocarbonyl)-2,4,6-triiodo-N-methylanilide 45.75 g (75 mmol) of 5-methylamino-2,4,6-triiodoisophthalic acid dichloride is dissolved in 450 ml of toluene, the solution is heated to 80° C. and 9.4 g (38 mmol) of benzyloxymalonic acid dichloride is added. The bisanilide precipitates out as crystals after a few minutes. After one hour it is cooled to room temperature, the precipitate is suctioned off, washed with toluene and dried in a vacuum at 50° C. 38.4 g (27.50 mmol)=73.5% of theory of the crystallizate is obtained. Melting point: greater than 350° C.

(2R,3R)-Di-O-benzoyltartaric acid bis[3,5-bis(chlorocarbonyl)-2,4,6-triiodo-N-methylanilide 30.4 g (50 mmol) of 5-methylamino-2,4,6-triiodoisophthalic acid dichloride is dissolved in 300 ml of toluene, the solution is heated to 80° C. and 21.93 g (25 mmol) of (2R,3R)-di-O-benzoyltartaric acid dichloride (produced similarly to D. Seebach et al. Ber. 1980, 1691) is added. The product begins to precipitate as crystals after a few minutes. After two hours it is cooled to room temperature, the precipitate is suctioned off, washed with toluene and dried in a vacuum at 50° C. 56.74 g (36.8 mmol)=73.6% of theory of crystallizate is obtained. Melting point: greater than 350° C.

EXAMPLE 1

Hydroxymalonic acid bis[3,5-bis(2,3-dihydroxypropylcarbomoyl)-2,4,6-triiodoanilide 263.5 g (200 mmol) acetoxymalonic acid bis[3,5-bis(chlorocarbonyl)-2,4,6-triiodoanilide] is dissolved in 1.32 liters of tetrahydrofuran and the solution is mixed at room temperature with 164 g (1.8 mol) of 1-aminopropanediol-2,3 dissolved in 100 mol of tetrahydrofuran. The product precipitates out with the hydrochloride of the amine. After a five-hour reaction time the reaction mixture is concentrated by evaporation under reduced pressure, the residue is dissolved in about 1 liter of water, adjusted to pH 12 at 50° C. with concentrated sodium hydroxide solution, stirred for about 30 minutes at this temperature, then neutralized with concentrated hydrochloric acid and desalted on ion exchangers. The aqueous eluate is concentrated to dryness by evaporation under reduced pressure. The yield is 257.9 g=172.6 mmol=86.3% of theory of hydroxymalonic acid bis[3,5-bis(2,3-dihydroxypropylcarbamoyl)-2,4,6-triiodoanilide].

Analysis: cal.: C 24.92 H 2.42 I 50.96 N 5.62 O 16.06
Fnd: C 25.13 H 2.61 I 50.67 N 5.43

EXAMPLE 2

Hydroxymalonic acid bis[3,5-bis(2,3-dihydroxy-N-methylpropylcarbamoyl)-2,4,6-triiodoanilide 263.5 g (200 ml) of acetoxymalonic acid bis[3,5-bis(chlorocarbonyl)-2,4,6-triiodoanilide is dissolved in 1.32 liters of tetrahydrofuran. 189 g (1.8 mol) of 1-methylaminopropanediol-2,3, dissolved in 100 ml of tetrahydrofuran, is instilled in this solution at room temperature. The product precipitates out together with the hydrochloride of the amine. After five-hour reaction time, the reaction mixture is concentrated by evaporation under reduced pressure, the residue is dissolved in about 1 liter of water, adjusted to pH 12 at 50° C. with sodium hydroxide solution, stirred for about 30 minutes at this temperature, then neutralized with concentrated hydrochloric acid and desalted on ion exchangers. The aqueous eluate is concentrated to dryness by evaporation under reduced pressure. The yield is 269.73 g=174 mmol=87% of theory of hydroxymalonic acid bis[3,5-bis(2,3-dihydroxy-N-methylpropylcarbamoyl)-2,4,6-triiodoanilide]

Analysis: Cal. C 27.11 H 2.86 I 49.11 N 5.42 O 15.48
Fnd: C 27.32 H 2.67 I 48.93 N 5.40

EXAMPLE 3

Hydroxymalonic acid bis[3,5-bis[(1RS,2SR)-2,3-dihydroxy-1-hydroxymethylpropylcarbamoyl]-2,4,6-triiodoanilide]

263.5 g (200 mmol) of acetoxymalonic acid bis[3,5-bis(chlorocarbonyl)-2,4,6-triiodoanilide] is dissolved in 1.32 liters of tetrahydrofuran and the solution of 239.74 g (1.8 mol) of 6-amino-2,2-dimethyl-1,3-dioxepin-5-ol, dissolved in 200 ml of tetrahydrofuran, is instilled at room temperature. After a five-hour reaction time the hydrochloride is suctioned off, the filtrate is concentrated by evaporation under reduced pressure, the residue is suspended in about 1 liter water, acidified at room temperature with concentrated hydrochloric acid to pH 1 and stirred for 5 hours, then adjusted to pH 12 with concentrated sodium hydroxide solution and stirred for 1 hour at 50° C., finally neutralized with concentrated hydrochloric acid and desalted on ion exchangers. The aqueous eluate is concentrated to dryness by evaporation under reduced pressure. The yield is 257 g=159.2 mmol=79.6% of theory of hydroxymalonic acid bis[3,5-bis[(1RS,2RS)-2,3-dihydroxy-1-hydroxymethyl-propylcarbamoyl]-2,4,6-triiodoanilide].

Analysis: Cal.: C 26.02 H 2.80 I 47.14 N 5.20 O 18.82
Fnd: C 26.23 H 2.88 I 46.95 N 5.13

EXAMPLE 4

Hydroxymalonic acid bis[3,5-bis(2,3-dihydroxypropylcarbamoyl)-2,4,6-triiodo-N-methylanilide 269.1 g (200 mol) acetoxymalonic acid bis[3,5-bis(-chlorocarbonyl)-2,4,6-triiodo-N-methylanilide] is dissolved in 1.32 liter tetrahydrofuran and 164 g (1.6 mol) of 1-aminopropanediol-2,3, dissolved in 100 ml of tetrahydrofuran, are instilled in this solution at room temperature. After five-hour reaction time the reaction mixture is concentrated by evaporation under reduced pressure, the residue is dissolved in about 1 liter of water, adjusted to pH 12 at 50° C. with concentrated sodium hydroxide solution, stirred for about 45 minutes at this temperature, then neutralized with concentrated hydrochloric acid and desalted on ion exchangers. The aqueous eluate is concentrated to dryness by evaporation under reduced pressure. The yield is 258.8 g=170 mmol=85% of theory of hydroxymalonic acid bis[3,5-bis(2,3-dihydroxypropylcarbamoyl)-2,4,6-triiodo-N-methylanilide]

Analysis: Cal.: C 26.04 H 2.64 I 50.02 N 5.52 O 15.76
Fnd: C 25.93 H 2.71 I 49.87 N 5.33

EXAMPLE 5

Hydroxymalonic acid bis[3,5-bis(2,3-dihydroxy-N-methylpropylcarbamoyl)-2,4,6-triiodo-N-methylanilide]

269.1 g (200 mol) of acetoxymalonic acid bis[3,5-bis(-chlorocarbonyl)-2,4,6-triiodo-N-methylanilide] is dissolved in 1.35 liters of tetrahydrofuran and 189.3 g (1.6 mol) of 1-methylaminopropanediol-2,3, dissolved in 100 ml of tetrahydrofuran, is instilled in this solution at room temperature. After five-hour reaction time, the reaction mixture is concentrated by evaporation under reduced pressure, the residue is dissolved in about 1 liter of water, adjusted to pH 12 at 50° C. with concentrated sodium hydroxide solution, stirred at this temperature for about 50 minutes, then neutralized with concentrated hydrochloric acid and desalted on ion exchangers. The aqueous eluate is concentrated to dryness by evaporation under reduced pressure. The yield is 162.6 g=166.4 mmol=83.2% of theory of hydroxymalonic acid bis[3,5-bis(2,3-dihydroxy-N-methylpropylcarbamoyl)-2,4,6-triiodo-N-methylanilide]

Analysis: Cal.: C 28.15 H 3.06 I 48.24 N 5.32 O 15.2
Fnd: 28.32 H 3.17 I 48.08 N 5.2

EXAMPLE 6

Hydroxymalonic acid bis[3,5-bis[(1RS,2SR)-2,3-dihydroxy-1-hydroxymethyl-propylcarbamoyl]-2,4,6-triiodo-N-methylanilide]

269.1 g (200 mmol) of acetoxymalonic acid bis[3,5-bis(chlorocarbonyl)-2,4,6-triiodo-N-methylanilide] id dissolved in 1.35 liters of tetrahydrofuran and 239.74 g (1.8 mol) of 6-amino-2,2-dimethyl-1,3-dioxepin-5-ol, dissolved in 200 ml of tetrahydrofuran, is instilled in this solution at room temperature. After five-hour reaction time, the hydrochloride is suctioned off, the filtrate is concentrated by evaporation under reduced pressure, the residue is suspended in about 1 liter of water, acidified to pH 1 at room temperature with concentrated hydrochloric acid and stirred 5 hours, then adjusted to pH 12 with concentrated sodium hydroxide solution and stirred for one hour at 50° C., then neutralized with concentrated hydrochloric acid and desalted on ion exchangers. The aqueous eluate is concentrated to dryness by evaporation under reduced pressure. The yield is 277.2 g=168.8 mmol=84.4% of theory of hydroxymalonic acid bis[3,5-bis(1RS,2SR)-2,3-dihydroxy-1-hydroxymethylpropylcarbamoyl]-2,4,6-triiodo-N -methylanilide]

Analysis: Cal.: C 27.06 H 2.94 I 46.36 N 5.11 O 18.51
Fnd: C 26.93 H 3.06 I 46.15 N 5.03

EXAMPLE 7

Methoxymalonic acid bis[3,5-bis(2,3-dihydroxypropylcarbamoyl)-2,4,6-triiodo-N-methylanilide]

262.35 g (200 mmol) of methoxymalonic acid bis[3,5-bis(chlorocarbonyl)-2,4,6-triiodo-N-methylanilide] is dissolved 1.32 liters of dioxane and 164 g (1.8 mol) of 1-aminopropanediol-2,3, dissolved in 100 ml of dioxane, is instilled in the solution at room temperature. After 3-hour reaction time the reaction mixture is concentrated by evaporation under reduced pressure, the residue dissolved in 800 ml of water and this solution is desalted on ion exchangers. After desalting, the aqueous eluate is concentrated to dryness by evaporation under reduced pressure. The yield is 262.07 g=170.6 mmol=85% of theory of methoxy malonic acid bis-[3,5-dihydroxypropylcarbamoyl)2,4,6-triiodo-N-methylanilide].

Analysis: Cal.: C 26.58 H 2.75 I 49.56 N 5.47 O 15.62
Fnd.: C 26.43 H 2.91 I 49.37 N 5.28

EXAMPLE 8

Methoxy malonic acid bis[3,5-bis(2,3-dihydroxypropylcarbamoyl)-2,4,6-triiodanilide]

128.95 g (100 mmol) of methoxy malonic acid bis[3,5-bis(chlorocarbonyl)-2,4,6-triiidoanilide] is dissolved in 644 ml of tetrahydrofuran and 87.5 g (960 mmol) of aminopropanediol-2,3, dissolved in 50 ml of tetrahydrofuran, is instilled into this solution at room temperature. After five-hour reaction under reduced pressure it is concentrated to a large extent, the residue is dissolved in water and desalted on ion exchangers. The eluate of the ion exchangers, which has been concentrated by evaporation, yields 129.9 g=86.3 mmol=86.3% of theory of amorphous methoxymalonic acid bis[2,3-bis(2,3-dihydroxypropylcarbamoyl)-2,4,6-triiodoanilide].

Analysis: Cal.: C 25.48 H 2.54 I 50.48 N 5.57 O 15.91
Fnd: C 25.63 H 2.71 I 50.26 N 5.32

EXAMPLE 9

Methoxymalonic acid bis[3,5-bis(2,3-dihydroxypropylcarbamoyl)-2,4,6-triiodo-N-methylanilide]

4.6 g (200 mmol) of sodium is dissolved in a mixture of 200 ml of methanol and 200 ml of propanediol-1,2, 75.4 g (50 mmol) of methoxymalonic acid bis[3,5- bis(2,3-dihydroxypropylcarbamoyl)-2,4,6-triiodoanilide] is added, stirred for 3 hours at 50° C., then the methanol is distilled off at normal pressure, the 21.3 g (150 mmol) of methyl iodide is added to the remaining solution and stirred for 24 hours at 50° C. The reaction solution is cooled to room temperature and stirred into 2 liters of methylene chloride. In this case the product precipitates out as pasty mass. It is decanted from this, dissolved in 200 ml of water and desalted on ion exchangers. 59.76 g (38.9 mmol)=77.8% of theory of methoxymalonic acid bis[3,5-bis(2,3-dihydroxypropylcarbamoyl)-2,4,6-triiodo-N-methylanilide] is obtained as amorphous solid.

Analysis: Cal.: C 26.58 H 2.75 I 49.56 N 5.47 O 15.62
Fnd: C 26.67 H 2.83 I 49.37 N 5.38

EXAMPLE 10

2,3-dihydroxysuccinic acid bis[3,5-bis(2-hydroxy-1-hydroxymethylethyl)-2,4,6-triidoanilide]

42.41 g (30 mmol) of 2,3-diacetoxysuccinic acid bis[3,5-bis(chlorocarbonyl)-2,4,6-triiodo-N-methylanilide] is suspended in 420 ml of acetone, 34.34 g (120 mml) of soda decahydrate and 13.67 g (150 mmol) of 2-aminopropanediol-1,3 are added, stirred for one hour at room temperature an d two hours at boiling temperature. It is then cooled to room temperature, the precipitate is suctioned off, extracted hot with 200 ml of ethanol, filtered, the ethanol and acetone filtrate are combined and concentrated by evaporation. The residue is dissolved in water, the acetate groups are saponified at pH 11 at 50° C. with sodium hydroxide solution, neutralized with hydrochloric acid, desalted on ion exchangers and the eluate is freeze-dried. The yield is 38.93 g=25.08 mmol=83.6% of theory of 2,3-dihydroxysuccinic acid bis[3,5-bis(2-hydroxy-1-hydroxymethylethyl)-2,4,6-triiodo-N-methylanilide]

Analysis: Cal. C 25.21 H 2.51 I 49.95 N 5.51 O 16.79
Fnd: C 25.07 H 2.73 I 49.7 N 5.32

EXAMPLE 11

Hydroxymalonic acid bis[3,5-bis(2-hydroxy-1-hydroxymethylethyl)-2,4,6-triiodoanilide]

(a) Benzyloxy malonic acid bis[3,5-bis(2-hydroxy-1-hydroxymethylethyl)-2,4,6-triido-N-(2-hydroxyethyl)-anilide]

68.3 (50 mmol) of benzyloxy malonic acid bis[3,5-bis(-chlorocarbonyl)-2,4,6-triiodoanilide] is dissolved in 140 ml of dimethylformamide, 25.3 g (250 mmol) of triethylamine is added and 22.78 g (250 mmol) of 2-aminopropanediol-1,3 is instilled at room temperature. It is stirred for 2 more hours, the precipitate of the triethylammonium chloride is suctioned off and the filtrate is instilled in 2 liters of dichloromethane. The solid amorphous precipitate is suctioned off, washed with dichloromethane and suspended in 300 ml of water at room temperature. It is stirred at room temperature for 24 hours, the solid is suctioned off, rewashed with a little water and dried in a vacuum for 60 hours at 50° C. 68.36 g (43.15 mmol)=86.3% of theory of the partially amorphous, partially crystalline solid is obtained.

Analysis: Cal.: C 28.81 H 2.67 I 48.06 N 5.30 O 15.14
Fnd: C 28.55 H 2.48 I 47.85 N 5.53

(b) hydroxymalonic acid bis[3,5-bis(2-hydroxy-1-hydroxymethylethyl)-2,4,6-triiodo-N-(2-hydroxyethyl)-anilide ]

4.83 g (210 mmol) of sodium is dissolved in a mixture of 200 ml of methanol and 200 ml of propanediol-1,2, 79.2 g (50 mmol) of the product of example 11a is added, the solution is stirred for 3 hours at 50° C. and the methanol is then distilled off at normal pressure. The reaction solution is then mixed with 16.43 g (200 mmol) of chloroethanol and stirred for 24 hours at 50° C. It is cooled to room temperature and instilled in 3 liters of acetone. The amorphous precipitate is suctioned off, washed with acetone and dried in a vacuum at 50° C. for 24 hours. The amorphous benzyloxy intermediate product is dissolved in 1 liter of ethanol during heating and 4.6 g (200 mmol) of sodium is added in portions at room temperature. The solution is then stirred for 12 hours at room temperature and then concentrated by evaporation to a considerable extent, the residue is dissolved in 150 ml of water, filtered and desalted on ion exchangers. 45.1 g (28.5 mmol)=57% of theory of the title compound is obtained as amorphous solid.

EXAMPLE 12

Hydroxymalonic acid bis[3,5-bis(2-hydroxy-1-hydroxymethylethyl)-2,4,6-triiodo-N-methylanilide]

81.94 g (60 mmol) of benzyloxymalonic acid bis[3,5-bis(chlorocarbonyl)-2,4,6-triiodo-N-methylanilide] is dissolved in 160 ml of dimethylformamide, 30.4 g (300 mmol) of triethylamine is instilled and 27.3 g (300 mmol) of 2-aminopropanediol-1,3 is instilled at room temperature. It is stirred for 2 hours at room temperature, the precipitate of triethylammonium chloride is suctioned off and the filtrate is precipitated in 2 liters of dichloromethane. The amorphous precipitate is suctioned off, washed with dichloromethane and dried in a vacuum for 24 hours at 50° C. The solid id dissolved in 1 liter of ethanol during heating, the solution is filtered and mixed with sodium by portions with a total of 6.9 g (300 mmol) at room temperature and then stirred for 12 hours at room temperature. It is then concentrated by evaporation to a very great extent, dissolved in 200 ml of water and desalted on ion exchangers. The corresponding eluate fractions yield, when concentrated by evaporation, 58.07 g (38.1 mmol)=63.5% of theory of the compound as solid.

Analysis: Cal. C 26.00 H 2.77 I 49.95 N 5.51 O 15.74
Fnd: C 26.18 H 2.93 I 49.72 N 5.39

EXAMPLE 13

2,3-Dihydroxysuccinic acid bis[3,5-bis[2,3-dihydroxypropylcarbonyl)-2,4,6-triiodo-N-methylanilide]

70.92 g (46 mmol) of (2R,3R-di-O-benzoyyltartaric acid bis[3,5-bis(chlorocarbonyl)-2,4,6-triiodo-N-methylanilide] is dissolved in 140 ml of dimethylformamide, 23.27 g (230 mmol) of triethylamine is added and 21 g (230 mmol) of 1-aminopropanediol-2,3 is instilled at room temperature. Then it is stirred for 2 hours at room temperature, then the precipitate of the triethylammonium chloride is suctioned off and the filtrate is precipitated in 2 liters of dichloromethane. The precipitate is suctioned off, washed with dichloromethane and suspended in 300 ml of water. This suspension is kept at 50° C. with sodium hydroxide solution at pH 10–11 until the pH no longer drops. A clear solution results. It is desalted on ion exchangers. The corresponding eluate fractions are collected and concentrated to dryness by evaporation. 55.9 g (36 mmol)=78.3% of theory is obtained as amorphous solid.

Analysis: Cal.: C 26.31 H 2.72 I 49.05 N 5.41 O 16.49
Fnd.: C 26.47 H 2.88 I 48.87 N 5.32

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A substituted dicarboxylic acid-bis(3,5-dicarbamoyl-2,4,6-triiodoanilide), of the formula

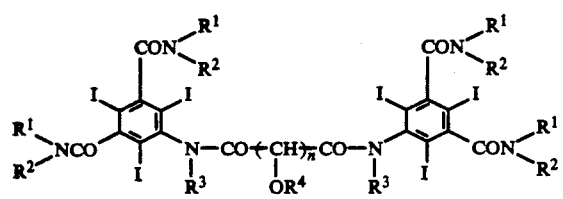

wherein
$R^1$ is hydrogen, a $C_1$–$C_4$ alkyl or $R^2$, wherein $R^1$ and $R^2$ may be the same or different,
$R^2$ is a straight-chain or branched-chain $C_2$–$C_8$ monohydroxyalkyl or polyhydroxyalkyl,
$R^3$ is a hydrogen atom, $C_1$–$C_4$ alkyl or $R^2$, wherein $R^2$ and $R^3$ are the same or different,
$R^4$ is a hydrogen atom, $C_1$–$C_4$ alkyl, and
n=1 or 2.

2. A compound of claim 1, wherein $R^1$ is methyl, ethyl, propyl or butyl.

3. A compound of claim 1, wherein $R^1$ is methyl.

4. A compound according to claim 1, wherein $R^2$ contains 1 to 5 hydroxy groups.

5. A compound according to claim 1, wherein $R^2$ contains 1–3 hydroxy groups.

6. A compound according to claim 1, wherein $R^2$ is 2-hydroxyethyl, 2-hydroxypropyl, 3-hydroxypropyl, 2,3-dihydroxypropyl, 1-hydroxymethyl-2-hydroxyethyl, 2,3-dihydroxybutyl, 2,4-dihydroxybutyl, 3,4-dihydroxybutyl, 3-hydroxy-2-(hydroxymethyl)-propyl, 2,3-dihydroxy-1-methylpropyl, 2-hydroxy-3-(hydroxymethyl)-butyl, 2,3,4-trihydroxybutyl, 2,4-dihydroxy-3-(hydroxymethyl)-butyl, 3-hydroxy-2,2-bis-(hydroxymethyl)-propyl, 4-hydroxy-3,3-bis-(hydroxymethyl)-butyl, 4-hydroxy-2,2-bis-(hydroxymethyl)-butyl, 2-hydroxy-1,1-bis-(hydroxymethyl)-ethyl, 1,3-dihydroxy-isopropyl, or 2,3-dihydroxy-1-hydroxy methyl propyl.

7. A compound according to claim 1, wherein $R^3$ is methyl, ethyl, propyl or butyl.

8. A compound according to claim 1, wherein $R^4$ is methyl, ethyl, propyl or butyl.

9. A compound according to claim 1, wherein $R^2$ is straight-chained containing 2 to 4 carbon atoms.

10. A compound according to claim 1, wherein $R^2$ is branched-chain containing 3 to 5 carbon atoms.

11. Hydroxymalonic acid bis[3,5-bis(2,3-dihydroxypropylcarbamoyl)-2,4,6-triiodoanilide]
hydroxymalonic acid bis[3,5-bis(2,3-dihydroxy-N-methylpropylcarbamoyl)-2,4,6-triiodoanilide
hydroxymalonic acid bis[3,5-bis[1RS,2SR)-2,3-dihydroxy-1-hydroxy-methylpropylcarbamoyl]-2,4,6-triiodoanilide]
hydroxy malonic acid bis[3,5-bis(2,3-dihydroxy-N-methylpropylcarbamoyl)-2,4,6-triodo-N-methylanilide]
hydroxymalonic acid bis[3,5-bis(2,3-dihydroxypropylcarbamoyl)-2,4,6-triiodo-N-methylanilide]
hydroxymalonic acid bis[3,5-bis[(1RS,2SR)-2,3-dihydroxy-1-hydroxymethylpropylcarbamoyl)-2,4,6-triiodo-N-methylanilide]
methoxymalonic acid bis[3,5-bis(2,3-dihydroxypropylcarbamoyl)-2,4,6-triiodo-N-methylanilide
methoxymalonic acid bis[3,5-bis(2,3-dihydroxypropylcarbamoyl)-2,4,6-triiodoanilide]
2,3,-dihydroxysuccinic bis[3,5-bis(2-hydroxy-1-hydroxymethylethyl)-2,4,6-triiodo-N-methylanilide
hydroxymalonic acid bis[3,5-bis(2-hydroxy-1-hydroxymethylethyl)-2,4,6-triiodo-N-(2-hydroxyethyl)anilide
hydroxymalonic acid bis[3,5-bis(2-hydroxy-1-hydroxymethylethyl)-2,4,6-triiodo-N-methylanilide
2,3-dihydroxysuccinic acid bis[3,5-bis(2,3-dihydroxypropylcarbamoyl)-2,4,6-triiodo-N-methylanilide], each a compound of claim 1.

12. A pharmaceutical composition comprising an effective amount of a compound of claim 1 and a pharmaceutically acceptable carrier.

13. A pharmaceutical composition comprising an effective amount of a compound of claim 11 and a pharmaceutically acceptable carrier.

14. A method of performing X-ray imaging of a patient comprising administering an effective amount of a compound of claim 1.

15. A method of performing X-ray imaging of a patient comprising administering an effective amount of a compound of claim 11.

16. A compound according to claim 1, wherein $R^4$ is methyl.

17. Methoxy malonic acid bis[3,5-bis(2,3-dihydroxypropylcarbamoyl)-2,4,6-triiodo-N-methylanilide], a compound of claim 1.

* * * * *